(12) United States Patent
Mizukami et al.

(10) Patent No.: US 8,101,414 B2
(45) Date of Patent: *Jan. 24, 2012

(54) REAGENT FOR SAMPLE ANALYSIS, REAGENT KIT FOR SAMPLE ANALYSIS AND METHOD FOR SAMPLE ANALYSIS

(75) Inventors: Toshihiro Mizukami, Halstenbek (DE); Hiroki Takeshita, Kobe (JP); Tatsuya Narikawa, Kobe (JP)

(73) Assignee: Sysmex Corporation, Hyogo (JP)

( * ) Notice: Subject to any disclaimer, the term of this patent is extended or adjusted under 35 U.S.C. 154(b) by 1172 days.

This patent is subject to a terminal disclaimer.

(21) Appl. No.: 11/763,827

(22) Filed: Jun. 15, 2007

(65) Prior Publication Data

US 2007/0298408 A1 Dec. 27, 2007

(30) Foreign Application Priority Data

Jun. 26, 2006 (JP) .................................. 2006-175716

(51) Int. Cl.
*G01N 33/48* (2006.01)

(52) U.S. Cl. .......................................... 436/10; 436/63

(58) Field of Classification Search ........ 435/4; 436/10, 436/63
See application file for complete search history.

(56) References Cited

U.S. PATENT DOCUMENTS

| | | | |
|---|---|---|---|
| 5,316,814 A | 5/1994 | Sawada et al. | |
| 5,445,853 A | 8/1995 | Hayashi et al. | |
| 5,518,928 A | 5/1996 | Cremins et al. | |
| 5,618,733 A | 4/1997 | Sakata et al. | |
| 5,631,165 A * | 5/1997 | Chupp et al. | 436/43 |
| 5,677,183 A | 10/1997 | Takarada et al. | |
| 6,004,536 A * | 12/1999 | Leung et al. | 424/9.6 |
| 6,168,844 B1 | 1/2001 | Takagishi et al. | |
| 6,664,110 B1 | 12/2003 | Tsuji et al. | |
| 7,101,678 B1 | 9/2006 | Montero-Julian et al. | |
| 7,332,295 B2 | 2/2008 | Valle | |
| 2002/0006631 A1 | 1/2002 | Houwen et al. | |
| 2007/0013906 A1 | 1/2007 | Kawate | |
| 2007/0254331 A1 | 11/2007 | Kawashima | |
| 2007/0287145 A1 | 12/2007 | Mizukami et al. | |

FOREIGN PATENT DOCUMENTS

| | | |
|---|---|---|
| EP | 0353393 A2 | 2/1990 |
| EP | 0895231 A2 | 2/1999 |
| EP | 0919008 A | 6/1999 |
| EP | 1 363 126 A1 | 11/2003 |
| JP | 05-040097 | 2/1993 |
| JP | 7-181177 | 7/1995 |
| JP | 08-338839 | 12/1996 |
| JP | 10-339729 A | 12/1998 |
| JP | 2002-148261 A | 5/2002 |
| JP | 2007-524771 A | 8/2007 |
| WO | 98/07061 A1 | 2/1998 |
| WO | 00/16103 A1 | 3/2000 |
| WO | 2005/085842 A2 | 9/2005 |

OTHER PUBLICATIONS

Aramendia, Pedro F. et al: "Temperature Dependence of Fluorescence and Photoisomerization in Symmetric Carbocyanines. Influence of Medium Viscosity and Molecular Structure" Journal of Physical Chemistry, vol. 98, No. 12, pp. 3165-3173, 1994.

Lepkowicz, Richard S. et al: "Femtosecond-to-nanosecond nonlinear spectroscopy of polymethine molecules" Journal of the Optical Society of America B: Optical Physics, vol. 22, No. 12, pp. 2664-2685, 2005.

Sims, P, J. et al: "Studies on the mechanism by which cyanine dyes measure membrane potential in red blood cells and phosphatidylcholine vesicles", Biochemistry, vol. 13, No. 16, Jul. 30, 1974, pp. 3315-3330.

\* cited by examiner

*Primary Examiner* — Shawquia Young
(74) *Attorney, Agent, or Firm* — Sughrue Mion, PLLC (57) ABSTRACT

A reagent for measuring a basophil and/or a nucleated red blood cell is described. The reagent comprises (a) an alcohol having 4 to 8 total carbon atoms, and (b) one or more fluorescent dyes selected from the group consisting of a compound of the general formula (I) and a compound of the general formula (II).

20 Claims, 5 Drawing Sheets

2-butanol
1%

Basophils

Nucleated red blood cells isoamyl alcohol
1%

Basophils

Nucleated red blood cells 2-phenoxyethanol
0.5%

Basophils

Nucleated red blood cells 2-phenylethanol
0.5%

Basophils

Nucleated red blood cells

REAGENT FOR SAMPLE ANALYSIS, REAGENT KIT FOR SAMPLE ANALYSIS AND METHOD FOR SAMPLE ANALYSIS

BACKGROUND OF THE INVENTION

1. Field of the Invention

The present invention relates to a reagent for sample analysis for analyzing a blood cell in a biological sample, a reagent kit for sample analysis for analyzing thereof, and a method for analyzing thereof.

2. Description of the Related Art

In the field of a clinical test, analysis of a blood cell in a sample is very useful for diagnosing various diseases of a circulatory organ or the like of a subject. Depending on a disease, the number of particular blood cells is increased or decreased, or blood cells which are not usually present appear in peripheral blood in some cases.

In recent years, a variety of automatic blood cell counting devices to which a principle of flow cytometry is applied are commercially available. Using such devices, classification and counting of a blood cell are performed in a general laboratory. When these automatic blood cell counting devices are used, classification and counting of leukocytes in a sample can be automatically performed.

In order to classify and count leukocytes, first, erythrocytes in a blood sample are lysed to prepare a measurement sample. By guiding the prepared measurement sample to a detector and detecting an electric impedance signal, leukocytes can be classified into three kinds. Meanwhile, a leukocyte usually includes the following five kinds; a lymphocyte, a monocyte, a neutrophil, an eosinophile, and a basophil. A leukocyte can be classified into five kinds by further performing fluorescence staining in addition to erythrocyte lysing treatment, irradiating the fluorescently stained blood cell with excitation light, detecting a fluorescent signal and a scattered light signal emitted from the stained blood cell, and analyzing it. Since a basophil is usually small in the number, a leukocyte can be more precisely classified into five kinds by the following method rather than by classification of a leukocyte into five kinds by one time measurement. Based on the property that a basophil is hardly destroyed under an acidic condition as compared with other leukocytes, the number of the basophil is measured by treating a blood sample exclusively for measuring a basophil (see U.S. Pat. No. 5,518,928). Then, by combining the result obtained from measurement of the number of the basophil and the result of leukocyte classification obtained by another method, a leukocyte can be classified into five kinds more precisely.

Here, a problem which frequently arises in leukocyte measurement is appearance of a nucleated red blood cell (NRBC). Since a nucleated red blood cell has a nucleus, a nucleus remains even when a red blood cell is lysing-treated. Thereby, since a nucleated red blood cell has a signal close to that of a lymphocyte in the aforementioned measurement, this gives a plus error at the time of measurement of the leukocyte number. In order to exclude this influence, treatment exclusively for measuring a nucleated red blood cell is performed to measure the nucleated red blood cell number (see U.S. Pat. No. 6,664,110), and the nucleated red blood cell number is subtracted from the leukocyte number obtained by another method, thereby, the precise leukocyte number can be obtained.

However, when a treatment exclusive for a particular blood cell is increased in order to perform precise leukocyte classification, it is laborious and there is a possibility that a device is complicated or is increased in size. In addition, when a plurality of reagents for exclusive use in particular blood cell measurement are used, the cost of a total blood test is increased. From such a viewpoint, it is preferable that a treatment exclusive for a particular blood cell is performed as little as possible.

Meanwhile, a basophil and a nucleated red blood cell can be measured by treating a blood sample under an acidic condition. Therefore, there is a possibility that, when a blood sample is treated under an acidic condition, there is a possibility that both of a basophil and a nucleated red blood cell can be measured by one time measurement. As one of such trials, Japanese Laid-Open Patent Application Publication No. 2002-148261 describes that a basophil and an erythroblast (nucleated red blood cell) can be measured by mixing a sample with an aqueous solution containing a red-blood cell dissolving agent and a surfactant which bring a leukocyte and an abnormal cell into a suitable state for staining, adding a staining solution containing a fluorescent dye to stain it, and measuring a fluorescent intensity and a scattered light intensity with a flow cytometer.

However, in the case of a specimen containing large number of leukocytes, the aforementioned conventional method does not sufficiently separate a basophil and a leukocyte other than a basophil in some cases.

SUMMARY OF THE INVENTION

The scope of the present invention is defined solely by the appended claims, and is not affected to any degree by the statements within this summary.

An object of the present invention is to provide a reagent for measuring sample and a method for measuring sample, which can more precisely differentiate and count a nucleated red blood cell and a basophil in a sample from other leukocytes.

A first aspect of the present invention is a reagent for measuring a basophil and/or a nucleated red blood cell, comprising:

(a) an alcohol having 4 to 8 total carbon atoms, and (b) one or more fluorescent dyes selected from the group consisting of a compound of the general formula (I):

(wherein $R^1$ and $R^2$ are independently an alkyl group;

$R^3$, $R^4$, $R^5$ and $R^6$ are independently a hydrogen atom or an alkyl group; and $X^-$ is an anion), and a compound of the general formula (II):

(wherein $R^7$ and $R^8$ are independently an alkyl group, wherein the alkyl group may have an acidic group which may form a salt;

$R^9$, $R^{10}$, $R^{11}$ and $R^{12}$ are independently a hydrogen atom or an acidic group which may form a salt; and at least one of $R^7$ to $R^{12}$ has an acidic group which has released a proton).

A second aspect of the present invention is a reagent kit for measuring a basophil and/or a nucleated red blood cell, comprising:

a first solution containing
an alcohol having 4 to 8 total carbon atoms and
a surfactant for hemolyzing a red blood cell and giving damage to a cell membrane of a leukocyte to such an extent that a fluorescent dye is capable of permeating therethrough, and a second solution containing one or more fluorescent dyes selected from the group consisting of a compound of the general formula (I) and a compound of the general formula (II).

A third aspect of the present invention is a method for analyzing sample, comprising the steps of:
staining a blood cell in the sample by using
an alcohol having 4 to 8 total carbon atoms and
one or more fluorescent dyes selected from the group consisting of a compound of the general formula (I) and a compound of the general formula (II);
irradiating the stained blood cell with light;
obtaining scattered light information and fluorescent information from the stained blood cell; and
counting a basophil and/or a nucleated red blood cell in the sample based on the scattered light information and the fluorescent information.

DESCRIPTION OF THE PREFERRED EMBODIMENTS

The present inventors conducted intensive studies and found out that it is possible to clearly differentiate a basophil from leukocytes other than a basophil by using a reagent for sample analysis, which contains an alcohol having 4 to 8 total carbon atoms together with a particular fluorescent dye.

The reagent for sample analysis, which is one embodiment of the present invention, is a reagent for measuring a basophil and/or a nucleated red blood cell. The reagent comprises the following (a) and (b).

(a) An alcohol having 4 to 8 total carbon atoms.

(b) One or more fluorescent dyes selected from the group consisting of a compound of the general formula (I):

(wherein $R^1$ and $R^2$ are independently an alkyl group;

$R^3$, $R^4$, $R^5$ and $R^6$ are independently a hydrogen atom or an alkyl group; and $X^-$ is an anion), and a compound of the general formula (II):

(wherein $R^7$ and $R^8$ are independently an alkyl group, wherein the alkyl group may have an acidic group which may form a salt;

$R^9$, $R^{10}$, $R^{11}$ and $R^{12}$ are independently a hydrogen atom or an acidic group which may form a salt; and at least one of $R^7$ to $R^{12}$ has an acidic group which has released a proton).

By using this reagent for sample analysis, it becomes possible to differentiate and count a nucleated red blood cell and a basophil from other blood cells more clearly. Thereby, it becomes possible to perform test and diagnosis of a disease more precisely. In measurement using the reagent, a nucleated red blood cell and a basophil can be counted by one time measurement. Depending on the test purpose, one of a nucleated red blood cell and a basophil have only to be measured in some cases. Even in such a case, only either one of a nucleated red blood cell and a basophil can be measured by using the reagent.

The basophil which can be measured by the reagent for sample analysis is a kind of leukocyte having a large acidic granule which can be stained with a basic dye. In addition, the nucleated red blood cell is generally also called an erythroblast, and includes a proerythroblast, a basophilic erythroblast, a polychromatophilic erythroblast and an orthochromatophilic erythroblast.

Herein, the "sample" refers to a body fluid sample collected from a mammal (preferably human). Such sample includes blood, marrow liquid and urine collected from a mammal (preferably human), as well as a sample collected from a mammal (preferably human) by apheresis or the like.

The reagent for sample analysis contains an alcohol having 4 to 8 total carbon atoms. Herein, the "alcohol having 4 to 8 total carbon atoms" means an alcohol having 4 to 8 total carbon atoms in one molecule. As the alcohol, an aliphatic alcohol having 4 to 8 total carbon atoms, which may be substituted with a phenyl group or a phenoxy group, is preferable. Examples of the alcohol include 1-butanol, 2-butanol, 1-pentanol, 2-pentanol, 3-pentanol, 1-hexanol, 2-hexanol, 3-hexanol, 1-heptanol, 2-heptanol, 3-heptanol, 1-octanol, 2-octanol, isobutanol (2-methyl-1-propanol), isoamyl alcohol (isopentyl alcohol), isooctyl alcohol, 2-phenylethanol, and 2-phenoxyethanol. An alcohol selected from the group consisting of 1-butanol, 2-butanol, 1-pentanol, 1-heptanol, isobutanol (2-methyl-propanl), isoamyl alcohol, 2-phenylethanol and 2-phenoxyethanol is preferable. These alcohols may be used alone, or two or more kinds may be used.

The reagent for sample analysis, by containing an alcohol having 4 to 8 total carbon atoms, has a more improved performance of differentiation between a basophil and leukocytes other than a basophil and differentiation of a nucleated red blood cell, as compared with the conventional reagent.

A concentration of the alcohol in the reagent can be appropriately selected depending on a kind of an alcohol used. The concentration of the alcohol is, for example, preferably 0.01 to 10% by weight, more preferably 0.01 to 5% by weight of the reagent. By inclusion of an alcohol in an amount in this range into the reagent, the performance of differentiation between a basophil and leukocytes other than a basophil, and differentiation of a nucleated red blood cell can be improved.

The fluorescent dye contained in the reagent for sample analysis is represented by the aforementioned general formulas (I) and (II).

Herein, the "alkyl group" in the general formulas (I) and (II) may be straight or branched. The alkyl group usually has 1 to 20 carbon atoms, preferably 1 to 10 carbon atoms. From a viewpoint of water solubility of the fluorescent dye, the alkyl group more preferably has 1 to 6 carbon atoms. Preferable examples of the alkyl group include methyl, ethyl, propyl, butyl, pentyl, and hexyl.

Examples of the anion $X^-$ in the general formula (I) include a halogen ion such as $F^-$, $Cl^-$, $Br^-$ and $I^-$, and $CF_3SO_3^-$, $BF_4^-$, and $ClO_4^-$.

Herein, the "acidic group" of the general formula (II) includes both of a group which can release a proton, and a group which has released a proton. Examples of the group which can release a proton include a carboxyl group, a sulfonic group, and a phosphoric group, and a carboxyl group or a sulfonic group is preferable.

The acidic group may form a salt. Examples of such salt include alkali metal salts such as a sodium salt, and a potassium salt, an ammonium salt, and an alkylammonium salt. A preferable salt is an alkali metal salt or an alkylammonium salt. More preferable is a sodium salt or a triethylammonium salt. That is, a preferable counter ion of the acidic group is an alkali metal ion or an alkylammonium ion, and a more preferable counter ion is a sodium ion or a triethylammonium ion.

The fluorescent dyes of the general formulas (I) and (II) can be used alone, or two or more kinds may be used.

The fluorescent dyes can be purchased from Hayashibara Biochemical Labs., Inc.

A concentration of the dye in the reagent can be appropriately selected depending on a kind of the dye. The concentration of the dye is generally 0.01 to 100 mg/L, preferably 0.1 to 10 mg/L, more preferably 0.3 to 6.0 mg/L.

When a blood cell is stained with the reagent for sample analysis, it is preferable to hemolyze a red blood cell which becomes an obstacle for measuring a nucleated red blood cell and a leukocyte (lymphocyte, monocyte, neutrophil, eosinophil, basophil), and give damage to a cell membrane of a nucleated red blood cell and a leukocyte. By this damage, permeability of a fluorescent dye into a nucleated red blood cell and a leukocyte is improved, and a blood cell can be effectively stained.

Usually, a pore is generated on a cell membrane of a red blood cell at an osmotic pressure of not higher than about 150 mOsm/kg. When hemoglobin in the red blood cell is eluted through the pore, the red blood cell becomes optically transparent (hemolyzed). The red blood cell which has become optically transparent does not substantially become an obstacle for measurement using flow cytometry. For hemolyzing a red blood cell, a low osmotic pressure condition and a low pH condition is preferable. An osmotic pressure satisfying these two conditions is 20 mOsm/kg to 150 mOsm/kg.

A pH of the reagent for sample analysis is preferably 2.0 to 4.5, more preferably 2.0 to 3.5. When the pH is within this range, a granule of a basophil is stabilized. In addition, a red blood cell can be effectively hemolyzed without excessively influencing on a leukocyte and a nucleated red blood cell. When a sample is treated at this pH, scattered light and fluorescent light of a non-nucleated red blood cell become extremely small, and does not substantially adversely influence on measurement of a nucleated red blood cell and a leukocyte.

The pH of the reagent may be adjusted using a buffer. A preferable buffer is a buffer having pKa around a desired pH±2.0. Examples of such buffer include citric acid, malic acid, diglycolic acid, malonic acid, and maleic acid.

A concentration of the buffer in the reagent is not particularly limited as far as it can retain the pH within the above range.

In order to adjust an osmotic pressure of the reagent for sample analysis within a suitable range for hemolyzing a red blood cell, an electrolyte such as NaCl and KCl, and sugars can be used. In addition, the osmotic pressure can be adjusted by a concentration of the buffer.

It is preferable that the reagent for sample analysis contains a surfactant which hemolyzes red blood cell, and gives damage to a cell membrane of a leukocyte to such an extent that the fluorescent dye can permeate therethrough. As the surfactant, a cationic surfactant is preferable. A more preferable cationic surfactant is a quaternary ammonium salt or a pyridinium salt type.

Examples of the preferable quaternary ammonium salt-type surfactant include a quaternary ammonium salt represented by the following formula.

[Chemical formula 1]

In the formula, $R^7$, $R^8$ and $R^9$ are a hydrogen atom, an alkyl group having 1 to 8 carbon atoms, or an aralkyl group having 6 to 8 carbon atoms. $R^7$, $R^8$ and $R^9$ may be the same or different. $R^{10}$ is an alkyl group having 8 to 18 carbon atoms, an alkenyl group having 8 to 18 carbon atoms, or an aralkyl group having 6 to 18 carbon atoms. $X^-$ is an anion.

In addition, examples of the preferable pyridinium salt-type surfactant include a pyridinium salt represented by the following formula.

[Chemical formula 2]

In the formula, $R^{11}$ is an alkyl group having 8 to 18 carbon atoms. $X^-$ is an anion.

These surfactants are known, and those described, for example, in Japanese Laid-Open Patent Application Publication No. 2002-148261 can be used.

Specific examples of the surfactant include decyltrimethylammonium bromide, dodecyltrimethylammonium chloride, octyltrimethylammonium bromide, octyltrimethylammonium chloride, lauryltrimethylammonium bromide, lauryltrimethylammonium chloride, myristyltrimethylammonium bromide, myristyltrimethylammonium chloride, and laurylpyridinium chloride.

A concentration of the surfactant in the reagent is preferably 10 to 10,000 mg/L, more preferably 100 to 5,000 mg/L. When the concentration is in this range, a red blood cell can be effectively hemolyzed without excessively influencing on a leukocyte and a nucleated red blood cell.

It is preferable that the reagent for sample analysis contains at least one kind of an organic acid having at least one aromatic ring in a molecule (hereinafter, referred to as "aromatic organic acid") or a salt thereof. Thereby, a red blood cell can be hemolyzed more effectively and in a short time. A preferable aromatic organic acid is salicylic acid or phthalic acid.

A concentration of the aromatic organic acid or a salt thereof in the reagent is not particularly limited as far as a pH of the reagent is within the above range. The concentration of the aromatic organic acid or a salt thereof is, for example, preferably 0.1 to 100 mM, more preferably 1 to 50 mM.

The reagent for sample analysis can be obtained by dissolving the fluorescent dye and the alcohol having 4 to 8 total carbon atoms in a suitable aqueous solvent to attain the aforementioned concentration. Alternatively, in a step of obtaining the reagent, optionally, the fluorescent dye and the alcohol having 4 to 8 total carbon atoms, as well as the surfactant and the aromatic organic acid or a salt thereof may be dissolved in a suitable aqueous solvent to attain the above concentration. In addition, in a step of obtaining the reagent, optionally, a pH may be adjusted using NaOH, HCl or the like.

The reagent for sample analysis may be obtained by mixing a solution of the fluorescent dye and a solution of the alcohol, each being dissolved in a suitable solvent, so that a final concentration of each component of them becomes in the aforementioned range. Alternatively, in a step of obtaining the reagent for sample analysis, optionally, a solution of the fluorescent dye and a solution of the alcohol, as well as a solution of the surfactant and a solution of the aromatic organic acid, each being dissolved in a suitable solvent, may be mixed so that a final concentration of each component of them falls within the above range. In addition, in a step of obtaining the reagent, optionally, a pH may be adjusted using NaOH, HCl or the like.

The suitable solvent is not particularly limited as far as it can dissolve these components. Examples of the suitable solvent include water, alcohol, ethylene glycol, dimethyl sulfoxide (DMSO), and a mixture thereof.

The reagent for sample analysis is mixed with a sample in such an amount that a volumetric ratio of the reagent: the sample is preferably 5 to 1000:1, more preferably 10 to 500:1. By mixing the reagent and the sample at such a ratio, lysis of a red blood cell proceeds rapidly, and staining of a blood cell can be performed well. When an amount of a sample is around a few µL to 100 µL, measurement can be performed well.

A reagent kit for sample analysis which is one embodiment of the present invention comprises the surfactant, the alcohol having 4 to 8 total carbon atoms, and the fluorescent dye. The reagent kit may contain a first reagent and a second reagent. It is preferable that the first reagent is a solution containing the surfactant and the alcohol having 4 to 8 total carbon atoms, and the second reagent is a solution containing the fluorescent dye. A solvent used in the first reagent or the second reagent is not particularly limited as far as it can dissolve the surfactant or the fluorescent dye. Examples of the solvent include water, an alcohol, an organic solvent (ethylene glycol, dimethyl sulfoxide (DMSO) etc.), and a mixture thereof. The fluorescent dye has low long term storage stability in an aqueous solution in some cases. In that case, it is preferable that the fluorescent dye is dissolved in the organic solvent.

The first reagent may contain the aromatic organic acid or a salt thereof. Alternatively, the reagent kit for sample analysis may further contain a third reagent containing an aromatic organic acid or a salt thereof in addition to the first reagent and the second reagent.

A method for analyzing sample which is one embodiment of the present invention comprises a step of staining a blood cell in a sample with the fluorescent dye and the alcohol having 4 to 8 total carbon atoms, a step of irradiating the stained blood cell with light, a step of obtaining scattered light information and fluorescent information from the stained blood cell, and a step of counting a basophil and/or a nucleated red blood cell in the sample based on the obtained scattered light information and fluorescent information. It is preferable that, in the staining step, a red blood cell is hemolyzed, damage is given to a cell membrane of a blood cell other than the hemolyzed red blood cell to such an extent that the fluorescent dye can permeate therethrough, and the damaged blood cell is stained.

In the staining step, the fluorescent dye, the alcohol having 4 to 8 total carbon atoms and the sample are mixed. In this step, preferably, the fluorescent dye, the alcohol having 4 to 8 total carbon atoms, the surfactant, and the sample are mixed. In this case, this surfactant gives damage to a cell membrane of a blood cell to such an extent that the fluorescent dye can permeate therethrough. For this reason, by mixing the surfactant and the sample, it becomes possible to effectively fluorescently stain a blood cell to be measured.

When the surfactant is used in the staining step, an order of mixing the surfactant, the fluorescent dye, the alcohol having 4 to 8 total carbon atoms, and the sample is not particularly limited. The surfactant, the fluorescent dye, and the alcohol having 4 to 8 total carbon atoms may be mixed in advance, and this mixed solution and the sample may be mixed. Alternatively, the surfactant and the sample may be mixed in advance, and this mixed solution, the fluorescent dye and the alcohol having 4 to 8 total carbon atoms may be mixed. Irrespective of the mixing order, an equivalent measuring result can be obtained.

In the staining step, the reagent for sample analysis may be mixed with the sample, or each component of the reagent kit for sample analysis may be mixed with the sample.

In the staining step, it is preferable that, after the fluorescent dye, the alcohol having 4 to 8 total carbon atoms, and the sample are mixed, they are reacted at a predetermined temperature for a predetermined time. A reaction temperature is preferably 15 to 50° C., more preferably 20 to 40° C. A reaction time is preferably 5 to 120 seconds, more preferably 5 to 30 seconds.

The blood cell stained in the staining step can be analyzed using a flow cytometer. Analysis of a blood cell using a flow cytometer will be explained below. By irradiating a blood cell with light when the stained blood cell passes through a flow cell of a flow cytometer, scattered light information and fluorescent information can be obtained. The scattered light information is not particularly limited as far as it is scattered light which can be measured with a commercially available general flow cytometer. Examples of the scattered light information include a pulse width and a scattered light intensity of scattered light such as forward scattered light (e.g. light receiving angle around 0 to 20 degrees), and side scattered light (light receiving angle around 90 degrees). Generally, it is known that side scattered light reflects internal information of a cell such as a nucleus and a granule of a cell. In addition, generally, it is known that forward scattered light reflects information of a size of a cell. It is preferable that, as the scattered light information, a forward scattered light intensity is used in the method for analyzing sample.

The fluorescent information is obtained by irradiating the measurement sample with light having a suitable wavelength, and measuring excited fluorescence. A suitable light receiving wavelength can be selected depending on the fluorescent dye used. Fluorescence is emitted from a nucleic acid and a granule in a cell which has been stained with the fluorescent dye.

A light source of a flow cytometer used is not particularly limited, but a light source having an appropriate wavelength for exciting the fluorescent dye is selected. As a light source of a flow cytometer, for example, a red semiconductor laser, a blue semiconductor laser, an argon laser, and a He—Ne laser are used. Particularly, since a semiconductor laser is very inexpensive as compared with a gas laser, it is suitable as a light source of a flow cytometer.

Figure 1:
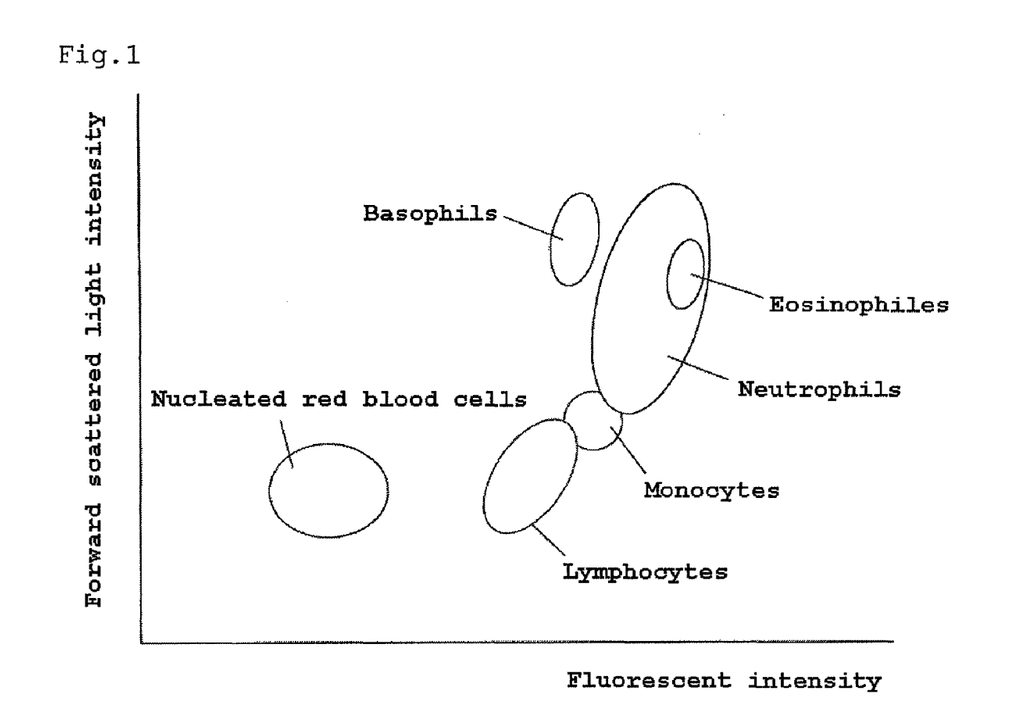
FIG. 1 is a schematic view of a scattergram obtained by analyzing a sample using a reagent for sample analysis, which is one embodiment of the present invention.

Based on the scattered light and the fluorescent light measured as described above, a nucleated red blood cell and a basophil can be differentiated from other blood cells and counted. It is preferable that this step comprises, for example, (1) producing a scattergram using fluorescent information and forward scattered light information as two axes, and (2) analyzing the obtained scattergram by suitable analysis software. When a scattergram is drawn using a fluorescent intensity on an X axis, and a forward scattered light intensity on a Y axis, for example, as shown in FIG. 1, each cell is distributed, forming a cluster. In such scattergram, N nucleated red blood cell has a smaller size than that of a granulocyte (neutrophil, eosinophil and basophil). Therefor, in such scattergram, it appears in a region in which a forward scattered light intensity is smaller than that of a granulocyte, and appears in a region in which a fluorescent intensity is smaller than that of a leukocyte. This can clearly differentiate a leukocyte and a nucleated red blood cell. In addition, a basophil appears in a region where a fluorescent intensity is smaller than that of an eosinophil and a neutrophil. This can clearly differentiate a basophil from other granulocytes. In addition, to which of a blood cell each cluster on a scattergram corresponds can be specified by treating a sample containing only each blood cell with the aforementioned reagent and, thereafter, performing measurement to confirm an appearance position of each cluster.

By analyzing a cluster on a scattergram with suitable analysis software, the number and a ratio of a nucleated red blood cell and a basophil can be calculated. Specifically, when a cluster is recognized at a position considered that a predetermined blood cell (provisionally referred to as blood cell A) appears in a scattergram, first, a center of this cluster is specified. Then, between from this center to an appearance region of a cluster of another blood cell (provisionally referred to as blood cell B), and up to a part where the predetermined blood cell A appears can be regarded as a boundary of the cluster of this blood cell A. A blood cell appearing in a set region can be counted as the predetermined blood cell A.

In addition, by counting also a leukocyte other than a basophil, a ratio of a basophil relative to a total leukocyte (basophil/total leukocyte: hereinafter, referred to as "basophil ratio"), and a ratio of a nucleated red blood cell relative to a total leukocyte (nucleated red blood cell/total leukocyte: hereinafter, referred to as "nucleated red blood cell ratio") can be calculated. A nucleated red blood cell ratio is usually expressed as a percentage of a nucleated red blood cell appearing per 100 leukocytes, and a unit is expressed by "number/100 WBC".

When the aforementioned reagent for sample analysis, reagent kit for sample analysis and method for analyzing sample are used, a cluster formed by a nucleated red blood cell, and a cluster formed by a basophil are clearly separated from a cluster formed by another blood cell, respectively. Therefore, a nucleated red blood cell and a basophil can be counted more precisely.

The following Examples illustrate the present invention in more detail, but various alterations and modifications are possible in the present invention, and the scope of the present invention is not limited by the following Examples.

EXAMPLES

Fluorescent dyes used in the following Examples are as follows.

[Chemical formula 3]

NK-3383

NK-9003

-continued

[Chemical formula 10]

NK-4249

[Chemical formula 11]

NK-3606

Comparative Example 1

Basophils contained in two blood samples collected from two subjects, respectively, were measured using an automatic hemocyte counting device XE-2100 (manufactured by Sysmex Corporation: carrying red semiconductor laser (633 nm)), and a basophil ratio was calculated. As a reagent, Stomatolyzer FBII (manufactured by Sysmex Corporation) was used.

As a result of a measurement, it was recognized that these samples had a high content of basophils (hereinafter, these samples are referred to as Baso sample 1 and Baso sample 2). A basophil ratio of the Baso sample 1 was 2.3%, and a basophil ratio of the Baso sample 2 was 1.2%. These results served as a control of Example 1.

Nucleated red blood cells contained in two specimens of blood samples collected from another two subjects, respectively, was measured using an automatic hemocyte counting device XE-2100, and a nucleated red blood cell ratio was calculated. As a reagent, Stomatolyzer NR (manufactured by Sysmex Corporation) was used.

As a result of a measurement, these samples were recognized that nucleated red blood cells appeared therein (hereinafter, these samples are referred to as NRBC sample 1 and NRBC sample 2). A nucleated red blood cell ratio of the NRBC sample 1 was 4.0 cells/100 WBC, and a nucleated red blood cell ratio of the NRBC sample 2 was 20.2 cells/100 WBC. These results served as a control of Example 1.

Example 1

Into a constant temperature bath at 35° C. was placed 1 mL of an aqueous solution containing 10 mM of salicylic acid (pH: 2.7), 2% of 1-butanol and 3000 ppm of DTAB. To this aqueous solution was added each dye (6 ppm of NK-3383, 2 ppm of NK-1840, 6 ppm of NK-2929, 6 ppm of NK-5056, 2 ppm of NK-9001, 2 ppm of NK-9002, 2 ppm of NK-9003, 2 ppm of NK-4249, and 2 ppm of NK-3606) described in FIG. 2 and FIG. 3 so that each concentration became the aforementioned concentration, respectively, to dissolve it, to obtain each reagent for sample analysis containing each dye.

One milliliter of the resulting reagent for sample analysis, and 20 μL of a blood sample (Baso sample 1 or 2, or NRBC sample 1 or 2) were sufficiently mixed. The resulting measurement sample was reacted for 20 seconds in a constant temperature bath (35° C.). After the reaction, the measurement sample was taken out from the constant temperature bath, and the measurement sample was guided to a detection part of a flow cytometer having a 633 nm excitation light source. Then, at the detection part, a blood cell in the measurement sample was irradiated with excitation light, and a scattered light signal and a fluorescent signal emitted from the blood cell were detected. The resulting signals were analyzed, and a basophil, a nucleated red blood cell and a total leukocyte were measured. This measurement was performed using an automatic hemocyte counting device XE-2100.

Measurement was performed by adding each of a reagent containing NK3383, a reagent containing NK1840, a reagent containing NK2929 and a reagent containing NK5056, to the Baso sample 1.

Measurement was performed by adding each of a reagent containing NK9001, a reagent containing NK9002, a reagent containing NK9003, a reagent containing NK4249, and a reagent containing NK3606, to the Baso sample 2.

Measurement was performed by adding each of a reagent containing NK3383, a reagent containing NK1840, a reagent containing NK2929 and a reagent containing NK5056, to the NRBC sample 1.

Measurement was performed by adding each of a reagent containing NK9001, a reagent containing NK9002, a reagent containing NK9003, a reagent containing NK4249, and a reagent containing NK3606, to the NRBC sample 2.

Figure 2:
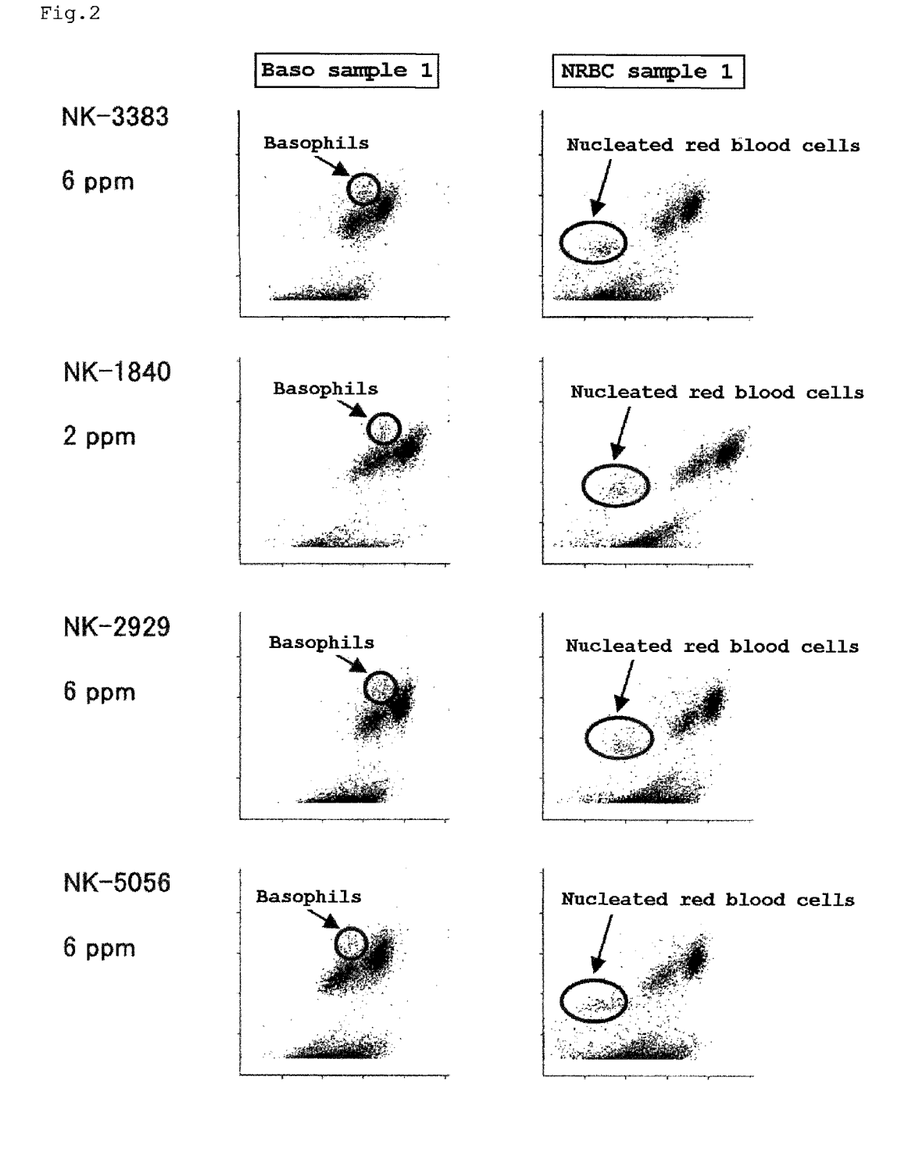
FIG. 2 shows scattergrams obtained analyzing a sample using a reagent for sample analysis of Example 1.
Figure 3:
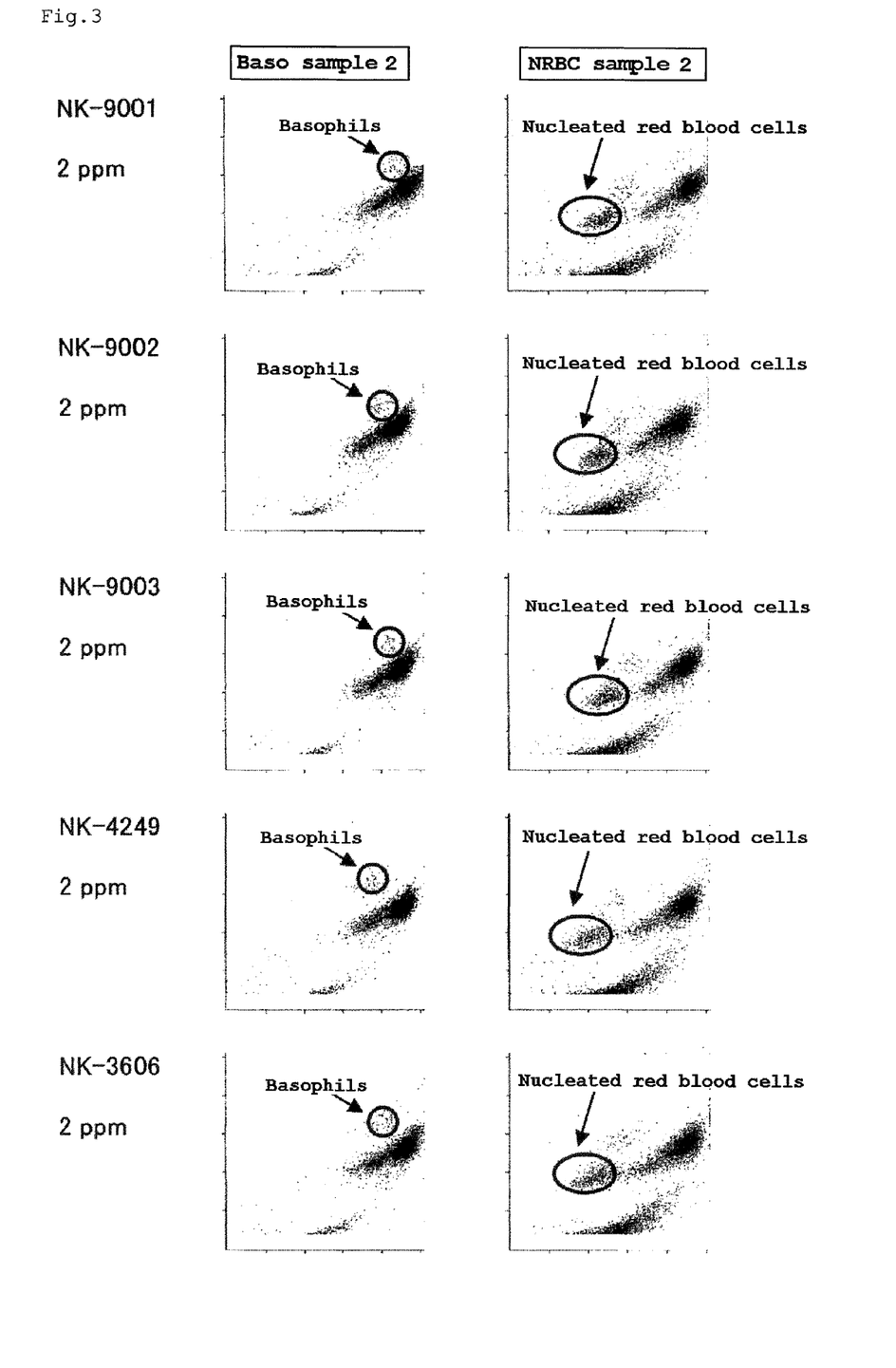
FIG. 3 shows scattergrams obtained by analyzing a sample using a reagent for sample analysis of Example 1.

For each measurement sample, a scattergram was produced using a fluorescent intensity and a forward scattered light intensity as two axes. The produced scattergrams are shown in FIG. 2 and FIG. 3. Based on the scattergrams of FIG. 2 and FIG. 3, a total leukocyte, a basophil and a nucleated red blood cell were counted, and a basophil ratio and a nucleated red blood cell ratio were calculated. Basophil ratios in the Baso samples calculated in Comparative Example 1 and the present Example are shown in Table 1, and nucleated red blood cell ratios in the NRBC samples calculated in Comparative Example 1 and the present Example are shown in Table 2.

TABLE 1

| Sample | Dye added to sample | Basophil ratio (%) Example 1 | Comparative Example 1 |
|---|---|---|---|
| Baso sample 1 | NK-3383 | 2.1 | 2.3 |
|  | NK-1840 | 2.1 |  |
|  | NK-2929 | 2.1 |  |
|  | NK-5056 | 1.6 |  |
| Baso sample 2 | NK-9001 | 1.2 | 1.2 |
|  | NK-9002 | 1.6 |  |
|  | NK-9003 | 1.2 |  |
|  | NK-4249 | 1.5 |  |
|  | NK-3606 | 1.6 |  |

TABLE 2

| Sample | Dye added to sample | Nucleated red blood cell ratio (Number/100WBC) | |
|---|---|---|---|
| | | Example 1 | Comparative Example 1 |
| NRBC sample 1 | NK-3383 | 5.2 | 4.0 |
| | NK-1840 | 4.2 | |
| | NK-2929 | 4.5 | |
| | NK-5056 | 4.7 | |
| NRBC sample 2 | NK-9001 | 19.5 | 20.2 |
| | NK-9002 | 20.0 | |
| | NK-9003 | 19.6 | |
| | NK-4249 | 19.4 | |
| | NK-3606 | 18.9 | |

As shown in FIGS. 2 and 3, it is seen that when the reagent for sample analysis of the present embodiment is used, a basophil is clearly differentiated from leukocyte components other than a basophil, and it is also seen that a nucleated red blood cell is clearly differentiated. Like this, a basophil and a nucleated red blood cell are clearly differentiated, respectively. For this reason, as shown in FIGS. 2 and 3, blood cells appearing in certain regions on a scattergram are handled as a basophil and a nucleated red blood cell, and the number and a ratio relative to the total leukocyte of them can be precisely obtained.

In addition, from Tables 1 and 2, a ratio calculated in Example 1 and a ratio calculated in Comparative Example 1 were approximate values. Therefore, it was confirmed that, when the reagent for sample analysis of the present embodiment is used, measurement can be performed at almost the same degree of precision as that obtained when a nucleated red blood cell and a basophil are measured using separate reagents (Comparative Example 1).

Example 2

Into a constant temperature bath at 35° C. was placed 1 mL of an aqueous solution containing 10 mM of salicylic acid (pH: 3.0) and 3000 ppm of decyltrimethylammonium bromide (DTAB). To this mixed solution was added each alcohol (0.05% of 1-heptanol, 2% of 1-pentanol, 2% of 1-butanol, 2% of isobutanol, 1% of 2-butanol, 1% of isoamyl alcohol, 0.5% of 2-phenoxyethanol, 0.5% of 2-phenylethanol) shown in FIG. 4 and FIG. 5 to attain the aforementioned concentration, respectively. Then, to each of the mixed solution was added a fluorescent dye NK-2929 to attain 6 ppm. To 1 mL of each of the resulting reagent for sample analysis was added 20 μL of a blood sample, followed by sufficiently mixing. The resulting measurement sample was reacted for 20 seconds in a constant temperature bath (35° C.). After the reaction, the measurement sample was taken out from the constant temperature bath, and was measured with a flow cytometer as in Example 1.

Figure 4:
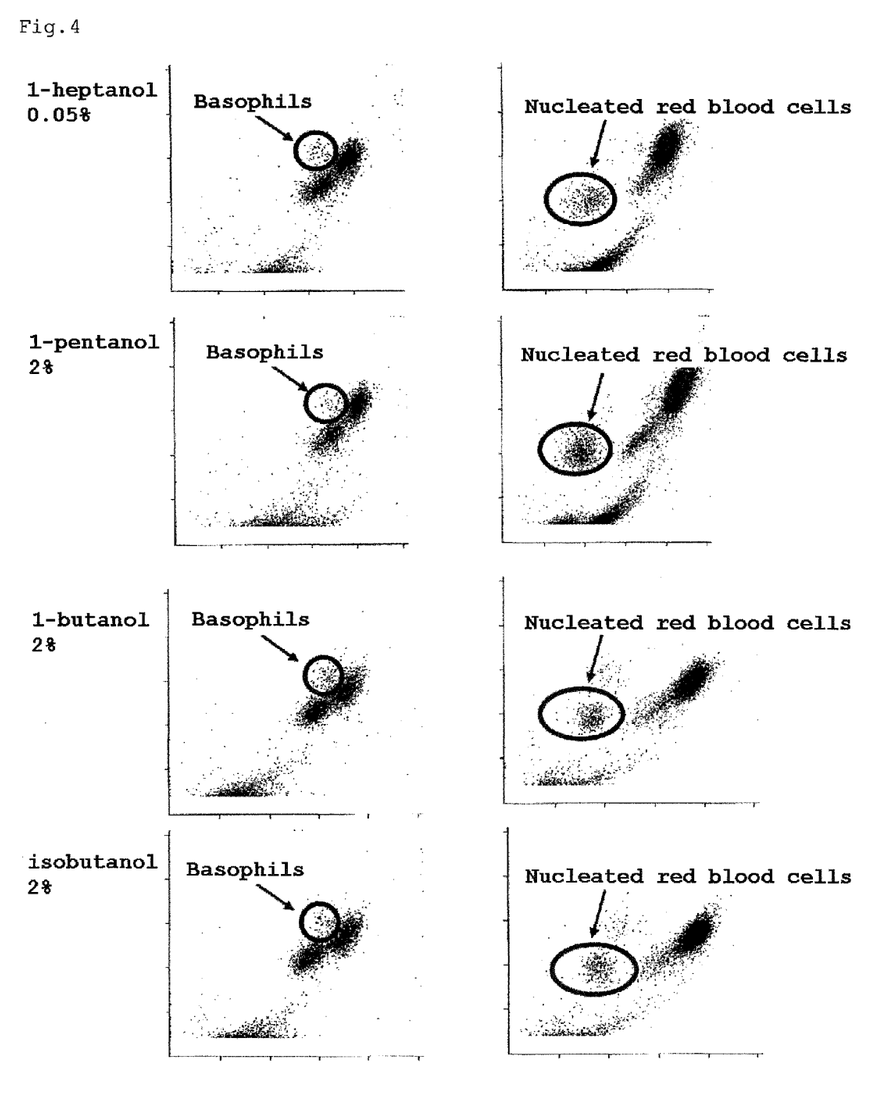
FIG. 4 shows scattergrams obtained by analyzing a sample using a reagent for sample analysis of Example 2.
Figure 5:
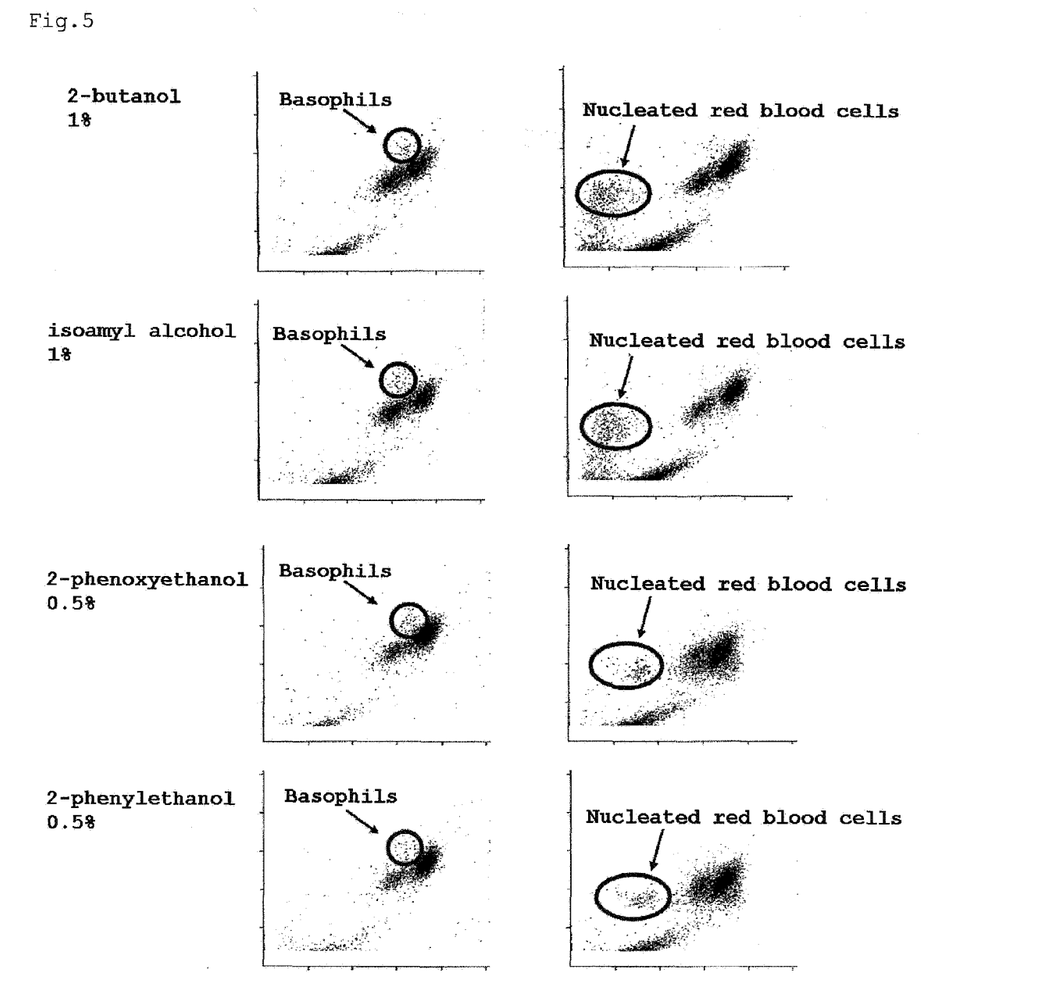
FIG. 5 shows scattergrams obtained by analyzing a sample using a reagent for sample analysis of Example 2.

For each measurement sample, a scattergram was produced using a fluorescent intensity and a forward scattered light intensity as two axes. The produced scattergrams are shown in FIG. 4 and FIG. 5. Based on the scattergrams of FIG. 4 and FIG. 5, a total leukocyte, a basophil and a nucleated red blood cell were counted, and a basophil ratio and a nucleated red blood cell ratio were calculated.

In addition, regarding the same sample as those used in the above measurement, a basophil ratio and a nucleated red blood cell ratio were measured using an automatic hemocyte counting device XE-2100 as described in Comparative Example 1.

These results are shown in Table 3 and Table 4. Table 3 shows the results on basophil ratios in samples and Table 4 shows nucleated red blood cell ratios in samples.

TABLE 3

| Dye added to sample | Alcohol added to sample | Basophil ratio (%) | |
|---|---|---|---|
| | | Example 1 | XE-2100 |
| NK-2929 | 1-Heptanol | 1.4 | 1.1 |
| | 1-Pentanol | 1.6 | 1.4 |
| | 1-Butanol | 2.5 | 2.9 |
| | Isobutanol | 2.4 | 2.9 |
| | 2-Butanol | 1.3 | 1.4 |
| | Isoamyl alcohol | 1.5 | 1.4 |
| | 2-Phenoxyethanol | 1.2 | 1.6 |
| | 2-Phenylethanol | 1.5 | 1.6 |

TABLE 4

| Dye added to sample | Alcohol added to sample | Nucleated red blood cell ratio (Number/100WBC) | |
|---|---|---|---|
| | | Example 1 | XE-2100 |
| NK-2929 | 1-Heptanol | 2.6 | 2.7 |
| | 1-Pentanol | 4.2 | 4.5 |
| | 1-Butanol | 6.3 | 5.8 |
| | Isobutanol | 6.1 | 5.8 |
| | 2-Butanol | 8.5 | 7.2 |
| | Isoamyl alcohol | 9.3 | 7.2 |
| | 2-Phenoxyethanol | 3.5 | 3.2 |
| | 2-Phenylethanol | 2.9 | 3.2 |

From the results of FIGS. 4 and 5 as well as Tables 3 and 4, it is seen that when a reagent for sample analysis, which contains an alcohol having 4 to 8 total carbon atoms, is used, a basophil is clearly differentiated from leukocyte components other than a basophil, and it is also seen that a nucleated red blood cell is clearly differentiated.

What is claimed is:

1. A reagent kit for measuring a basophil and/or a nucleated red blood cell, comprising:

a first solution containing an alcohol having 4 to 8 total carbon atoms, the concentration of the alcohol in the first solution being 0.01 to 10% by weight and a surfactant for hemolyzing a red blood cell and giving damage to a cell membrane of a leukocyte to such an extent that a fluorescent dye is capable of permeating therethrough, and a second solution containing one or more fluorescent dyes selected from the group consisting of a compound of the general formula (I):

(I)

[Structure of general formula (I): cyanine-type dye with rings A₁ and A₂, N-R¹ and N-R², pentamethine bridge, counter ion X⁻]

(wherein R¹ and R² are independently an alkyl group,

[A₁ group definitions:]

is [ring A₁ with methyl] or [substituted phenyl with R³] or [substituted naphthyl with R⁴],

[A₂ group definitions:]

is [ring A₂ with methyl] or [substituted phenyl with R⁵] or [substituted naphthyl with R⁶], R³, R⁴, R⁵ and R⁶ are independently a hydrogen atom or an alkyl group, and X⁻ is an anion), and a compound of the general formula (II):

(II)

[Structure of general formula (II): cyanine-type dye with rings A₃ and A₄, N-R⁷ and N-R⁸, pentamethine bridge]

(wherein R⁷ and R⁸ are independently an alkyl group, wherein the alkyl group may have an acidic group which may form a salt:

[A₃ group definitions:]

is [ring A₃ with methyl] or [substituted phenyl with R⁹] or [substituted naphthyl with R¹⁰],

[A₄ group definitions:]

is [ring A₄ with methyl] or [substituted phenyl with R¹¹] or [substituted naphthyl with R¹²], R⁹, R¹⁰, R¹¹ and R¹² are independently a hydrogen atom or an acidic group which may form a salt, and at least one of R⁷ to R¹² has an acidic group which has released a proton).

2. The reagent kit according to claim 1, wherein the first solution contains an aromatic organic acid.

3. The reagent kit according to claim 1, wherein the alcohol is selected from the group consisting of butanol, pentanol, heptanol, isobutanol, isoamyl alcohol, 2-phenylethanol and 2-phenoxyethanol.

4. The reagent kit according to claim 1, wherein an acidic group of the general formula (II) is a carboxyl group or a sulfonic group.

5. The reagent kit according to claim 1, wherein a counter ion of an acidic group forming a salt of the general formula (II) is an alkali metal ion or an alkylammonium ion.

6. The reagent kit according to claim 1, wherein the surfactant is a cationic surfactant.

7. The reagent according to claim 6, wherein the cationic surfactant is the type of a quaternary ammonium salt or a pyridinium salt.

8. The reagent kit according to claim 2, wherein the aromatic organic acid is selected from the group consisting of salicylic acid, salicylate, phthalic acid and phthalate.

9. The reagent kit according to claim 1, wherein the first solution has a pH of 2.0 to 4.5.

10. The reagent kit according to claim 1, wherein the second solution contains an organic solvent.

11. A method for analyzing sample using a reagent kit according to claim 1, comprising the steps of:
staining a blood cell in the sample by using an alcohol having 4 to 8 total carbon atoms and one or more fluorescent dyes selected from the group consisting of a compound of the general formula (I) and a compound of the general formula (II);
irradiating the stained blood cell with light;
obtaining scattered light information and fluorescent information from the stained blood cell; and
counting a basophil and/or a nucleated red blood cell in the sample based on the scattered light information and the fluorescent information.

12. The method according to claim 11, wherein the sample is mixed with the alcohol and the fluorescent dye in the staining step.

13. The method according to claim 11, in the staining step, further using a surfactant for hemolyzing a red blood cell and giving damage to a cell membrane of a leukocyte to such an extent that a fluorescent dye is capable of permeating therethrough.

14. The reagent kit according to claim 1, the concentration of the alcohol being 0.01 to 5% by weight.

15. The reagent kit according to claim 1, at least one R¹ and R² having 1 to 4 carbons, and at least one of R⁷ and R⁸ having 1 to 4 carbons.

16. The reagent kit according to claim 7, the quaternary ammonium salt being represented by

(wherein $R^{13}$, $R^{14}$, and $R^{15}$ are independently a hydrogen atom, an alkyl group having 1 to 8 carbon atoms, or an aralkyl group having 6 to 8 carbon atoms, $R^{16}$ is an alkyl group having 8 to 18 carbon atoms, an alkenyl group having 8 to 18 carbon atoms, or an aralkyl group having 6 to 18 carbon atoms, and $X^-$ is an anion).

17. The reagent kit according to claim 7, the pyridinium salt being represented by

(wherein $R^{17}$ is an alkyl group having 8 to 18 carbon atoms, and $X^-$ is an anion.

18. A reagent kit for measuring a basophil and/or a nucleated red blood cell, comprising:
   a first solution containing
      an alcohol having 4 to 8 total carbon atoms, the concentration of the alcohol in the first solution being 0.01 to 10% weight, and
      a cationic surfactant for hemolyzing a red blood cell and giving damage to a cell membrane of a leukocyte to such an extent that a fluorescent dye is capable of permeating therethrough, the surfactant being a quaternary ammonium salt or a pyridinium salt, and
   a second solution containing
      one or more fluorescent dyes selected from the group consisting of a compound of the general formula (I):

(wherein $R^1$ and $R^2$ are independently an alkyl group;

$R^3$, $R^4$, $R^5$ and $R^6$ independently a hydrogen atom or an alkyl group; and

$X^-$ is an anion), and a compound of the general formula (II):

(wherein $R^7$ and $R^8$ are independently an alkyl group, wherein the alkyl group may have an acidic group which may form a salt;

$R^9$, $R^{10}$, $R^{11}$ and $R^{12}$ are independently a hydrogen atom or an acidic group which may form a salt; and at least one of $R^7$ to $R^{12}$ has an acidic group which has released a proton).

19. The reagent kit according to claim 18, the quaternary ammonium salt being represented by (wherein $R^{13}$, $R^{14}$, and $R^{15}$ are independently a hydrogen atom, an alkyl group having 1 to 18 carbon atoms, or an aralkyl group having 6 to 8 carbon atoms, $R^{16}$ is an alkyl group having 8 to 18 carbon atoms, an alkenyl group having 8 to 18 carbon atoms, or an aralkyl group having 6 to 18 carbon atoms, and $X^-$ is an anion).

20. The reagent kit according to claim 18, the pyridinium salt being represented by (wherein $R^{17}$ is an alkyl group having 8 to 18 carbon atoms, and $X^-$ is an anion.

* * * * *